(12) United States Patent
Halachmi et al.

(10) Patent No.: US 12,137,671 B2
(45) Date of Patent: Nov. 12, 2024

(54) SYSTEM FOR MEASURING BODY TEMPERATURE IN POULTRY

(71) Applicant: The State of Israel, Ministry of Agriculture & Rural Development, Agricultural Research Organization (ARO), Rishon Lezion (IL)

(72) Inventors: Ilan Halachmi, Kfar Yehoshua (IL); Shelly Druyan, Pinski Street (IL); Natan Meir Barchilon, Rehovot (IL); Shlomo Yhahav, Rehovot (IL)

(73) Assignee: The State of Israel, Ministry of Agriculture & Rural Development, Agricultural Research Organization (ARO), Rishon Lezion (IL)

( * ) Notice: Subject to any disclaimer, the term of this patent is extended or adjusted under 35 U.S.C. 154(b) by 838 days.

(21) Appl. No.: 17/293,201

(22) PCT Filed: Nov. 14, 2019

(86) PCT No.: PCT/IL2019/051240
§ 371 (c)(1),
(2) Date: May 12, 2021

(87) PCT Pub. No.: WO2020/100140
PCT Pub. Date: May 22, 2020

(65) Prior Publication Data
US 2022/0000077 A1    Jan. 6, 2022

Related U.S. Application Data

(60) Provisional application No. 62/760,956, filed on Nov. 14, 2018.

(51) Int. Cl.
*A01K 29/00* (2006.01)
*A01K 31/20* (2006.01)
(Continued)

(52) U.S. Cl.
CPC .............. *A01K 29/00* (2013.01); *A01K 31/20* (2013.01); *A01K 39/01* (2013.01); *A61B 5/0008* (2013.01);
(Continued)

(58) Field of Classification Search
CPC ...... A01K 1/031; A01K 1/0047; A01K 31/22; A01K 31/20
See application file for complete search history.

(56) References Cited

U.S. PATENT DOCUMENTS 3,601,096 A * 8/1971 Rutherford .......... A01K 1/0064
119/448
4,369,030 A * 1/1983 Siccardi .................. F24H 15/20
432/222

(Continued)

FOREIGN PATENT DOCUMENTS

CN        104188635 A     12/2014
CN        105700596 A     6/2016
(Continued)

OTHER PUBLICATIONS

Chinese National Intellectual Property Administration, The Second Office Action for Chinese Invention Application No. 201980088450.1, dated Mar. 8, 2023, 30pp.
(Continued)

*Primary Examiner* — Yvonne R Abbott-Lewis
(74) *Attorney, Agent, or Firm* — The Roy Gross Law Firm, LLC; Roy Gross (57) ABSTRACT

An arrangement for measuring the body temperature of a bird comprises: (a) an enclosure having at least one aperture configured for receiving a bird's head thereinto at least in a partial manner; (b) at least one receptacle mounted within the enclosure; at least one receptacle accommodating an attractor; (c) at least one remote sensing instrument config-
(Continued)

ured for acquire thermal reading and calculating bird's temperatures. The remote sensor instrument and the receptacle accommodating the attractor are mutually disposed such that at least the bird's head is within a field of view of the remote sensor instrument.

20 Claims, 6 Drawing Sheets

(51) Int. Cl.
    *A01K 39/01*     (2006.01)
    *A61B 5/00*     (2006.01)
    *A61B 5/01*     (2006.01)
(52) U.S. Cl.
    CPC .......... *A61B 5/015* (2013.01); *A61B 2503/40* (2013.01); *A61B 2562/0271* (2013.01)

(56) References Cited

U.S. PATENT DOCUMENTS

| | | | |
|---|---|---|---|
| 4,524,722 A * | 6/1985 | Siccardi | A01K 31/22 119/448 |
| 4,535,601 A * | 8/1985 | Newell, Jr. | A01K 1/0047 165/254 |
| 4,700,887 A | 10/1987 | Timmons | |
| 8,590,487 B1 * | 11/2013 | Goddard, Jr. | A61B 6/527 119/751 |
| 8,733,290 B2 * | 5/2014 | Gerashchenko | A01K 1/031 119/421 |
| 8,789,494 B2 * | 7/2014 | Thompson | A01J 5/0132 119/14.02 |
| 9,282,725 B2 | 3/2016 | Jensen-Jarolim et al. | |
| 9,955,672 B2 | 5/2018 | Cook et al. | |
| 9,961,883 B2 | 5/2018 | Schaefer et al. | |
| 11,553,687 B2 * | 1/2023 | Roberson | A01K 1/0064 |

FOREIGN PATENT DOCUMENTS

| | | |
|---|---|---|
| CN | 07549049 A | 1/2018 |
| CN | 107549049 A | 1/2018 |
| EP | 0815726 A2 | 1/1998 |
| JP | 2017192315 A | 10/2017 |
| WO | 9523336 A1 | 8/1995 |
| WO | 2004105474 A1 | 12/2004 |
| WO | 2008001367 A1 | 1/2008 |
| WO | 2019027319 A1 | 2/2019 |

OTHER PUBLICATIONS

Intellectual Property India, Examination Report for Application No. 202147025750, dated Mar. 1, 2023, 6pp.
International Search Report for PCT Application No. PCT/IL2019/051240 dated Mar. 4, 2020, 5 pp.
Influence of environmental factors on infrared eye temperature measurements in cattle, Research in Veterinary Science, 96(1), 220-226. doi:10.1016/j.rvsc.2013.11.006 Church, J. S et al Jan. 1, 2014 (Jan. 1, 2014) Abstract, section 2.2.
Automatic broiler temperature measuring by thermal camera, doi. org/10.1016/j.biosystemseng.2019.08.011 , Biosystems Engineering Bloch et al. Jan. 1, 2019 (Jan. 1, 2019) The whole document.
International Written Opinion for PCT Application No. PCT/IL2019/051240 dated Mar. 4, 2020, 4 pp.
International Preliminary Report on Patentability for PCT Application No. PCT/IL2019/051240 dated Mar. 4, 2020, 5 pp.
Cloacal and Surface Temperatures of Broilers Subject To Thermal Stress, Engenharia Agricola, 37(5), 877-886, Journal of the Brazilian Association of Agricultural Engineering, ISSN: 1809-4430 Doi:http://dx.doi.org/10.1590/1809-4430-Eng.Agric.v37n5p877-886/2017 Abreu et al. Sep. 1, 2017 (Sep. 1, 2017) The whole document.
Challenges of measuring body temperatures of free-ranging birds and mammals, Anim Biotelemetry (2015) 3:33, DOI 10.1186/s40317-015-0075-2, Animal Biotelemetry McCafferty et al Jan. 1, 2015 (Jan. 1, 2015) The whole document.
Development of a temperature measurement system for a broiler flock with thermal imaging. Engineering in Agriculture, Environment and Food, 9(3), 291-295. doi: 10.1016/j.eaef.2016.03.001 Shen, P.-N. et al Jan. 1, 2016 (Jan. 1, 2016) The whole document.
Infrared Thermography—Applications in Poultry Biological Research, Infrared Thermography, Dr. Raghu V Prakash (Ed.), ISBN: 978-953-51-0242-7, InTech, Available from: http://www.intechopen.com/books/infrared-thermography/infrared-thermography-applications-in-agricultureand-biological-research, https://cdn.intechopen.com/pdfs/32032/InTech-Infrared_thermography_applications_in_poultry_biological_research.pdf, S. Yahav and M. Giloh Mar. 14, 2012 (Mar. 14, 2012) The whole document.
Chick Temperature, https://www.hatchability.com/Chick-temperature.php, 2017.
Marelli, Thermography: a non invasive method to investigate thermoregulation as welfare indicator in Naked Neck proiler chickens, Quantitative InfraRed Thermography, Jun. 2012, Italy.
Chinese Office Action Application No. 201980088450, Mar. 9, 2002, pp. 40.
Yahav, S, Infrared Thermography, Applications in Poultry Biological Research, Infrared Thermography, Mar. 14, 2012, InTech, XP055708519, pp. 93-112, DOI: 10.5772/27788.
Yahav. S, Sensible heat loss: the broiler's paradox, World's Poultry Science Journal, Dec. 12, 2004, pp. 419-434.
Giloh, Skin surface temperature of broiler chickens is correlated to body core temperature and is indicative of their thermoregulatory status, Poultry Science, vol. 91, Issue 1, Jan. 1, 2012, pp. 175-188.
European Search Report for International Application No. EP 19885712, mailed Nov. 16, 2021, 17pp.
Tüller R., 1999: Faustzahlen am Geflügelmast. In: Jahrbuch für die Geflügelwirtschaft 1999. J. Petersen (ed.), Verlag Ulmer, Stuttgart, p. 97.

* cited by examiner

SYSTEM FOR MEASURING BODY TEMPERATURE IN POULTRY

CROSS REFERENCE TO RELATED APPLICATIONS

This is a National Phase Patent Application which claims priority and the benefit to PCT Patent Application PCT/IL2019/051240 filed Nov. 14, 2019 and claims benefit to U.S. Provisional Patent application No. 62/760,956 filed Nov. 14, 2018, which is incorporated by reference herein in its entirety.

FIELD OF THE INVENTION

The present invention generally pertains to means and methods for measuring body temperatures in poultry.

BACKGROUND OF THE INVENTION

In the last decades, significant development has been done in the genetic selection of the meat-type broiler. These changes have led to rapid growth caused by increased feed efficiency and metabolic rate as well as increased heat production in broiler. However, inferior changes have led to a low capability in maintaining adequate dynamic steady-state mechanisms, under extreme environmental conditions. Thus, exposure of broilers to heat stress results in economic losses caused by longer time needed to reach marketing weight leading to poorer feed conversion and overall lower efficiency of poultry meat production. Sensors distributed in the farm space provide mean values of temperature and humidity, thus, they might present incorrect information about what the broiler actually feel. Extreme thermal conditions may dramatically affect the performance of broilers and other domestic animals, thereby impairing animal welfare and causing economic losses. Although body core temperature is the parameter that best reflects a bird's thermal status, practical and physiological obstacles make it irrelevant as a source of information on the thermal status of commercial flocks. Advances in the technology of infrared thermal imaging have enabled highly accurate, noncontact, and noninvasive measurements of skin surface temperature. This technology enables acquisition of reliable information on the thermal status of animals, thereby improving diagnoses of environmental stress in a flock.

An apparatus and method for facial temperature evaluation using thermal camera (Yahav et al., 2005), is being automatically implemented in this system. Temperature measurement of the individual broiler is of importance for improving climate control system in production house (Giloh et al., 2012).

Poultry welfare is measured in the ambient, namely at the environment within the poultry house. Hence for example, according to the recommendations of Tüller, newly hatched chicks require ambient temperatures of 32 to 35° C., see Tüller R., 1999: Faustzahlen am Geflügelmast. In: Jahrbuch für die Geflügelwirtschaft 1999. J. Petersen (ed.), Verlag Ulmer, Stuttgart, p. 97, incorporated herein as a reference. Alternatively, poltery temperature is detected by invasive manner, i.e., via measuring of cloaca temperature with a small rectal thermometer, see currently available link: https://www.hatchability.com/Chick-temperature.php incorporated herein as a reference. The normal body temperature of a bird is 41° C. A bird is most comfortable and grows faster in ambient temperatures ranging from 10° C. to 20° C. or more. These temperatures are those measured inside the poultry house, at bird level. The bird can tolerate and adapt to temperatures of 20-25° C. but above this heat stress is evident. Thermal analysis of the whole birds' body is known in the art, see Marelli, S. P., et al. "Thermography, a non-invasive method to investigate thermo regulation as welfare indicator in naked neck broiler chickens." 11th International Conference on Quantitative Information for Red Thermography. 2012, providing for a wide temperature variability. Hence, indirect temperature measurements of ambient in poultry house is not accurate, and is about 20° C. lower than the temperature of the animal itself. Such an indirect and non-accurate measurement leads to many drawbacks, such as decreasing animals' welfare.

CN107549049 The invention relates to an automatic cage-rearing chicken health state monitoring device, and belongs to the technical field of poultry raising. The technical effect that the health state of chicken individuals is judged through the number and body temperature, detected by the automatic cage-rearing chicken health state monitoring device, of the chicken individuals, and missing inspection of manual inspection is avoided. According to the technical scheme for achieving the technical effect, the automatic cage-rearing chicken health state monitoring device comprises a vidicon, a thermal imagery camera, an inspection device, an image processing module, a display module and an alarm, wherein the vidicon and the thermal imagery camera are arranged on the inspection device, the output end of the vidicon and the output end of the thermal imagery camera are electrically connected with the image processing module, and the output end of the image processing module is electrically connected with the display module and the alarm. The automatic cage-rearing chicken health state monitoring device can be widely applied to the field of poultry raising.

There is an unmet need for direct (namely, of a specific predefined organ of the animal), local, reproducible, at least semi-continuous, noncontact and non-invasive temperature measurements of birds in a poultry house.

SUMMARY OF THE INVENTION

It is an object of the present invention to provide an arrangement for measuring the body temperature of a bird, the system characterized by: (a) an enclosure comprising having at least one aperture configured for receiving a bird's head thereinto at least in a partial manner; (b) at least one receptacle mounted within said enclosure; said at least one receptacle accommodating an attractor; and (c) at least one remote sensing instrument, e.g., an infrared thermal sensor, configured for acquire thermal reading and calculating bird's temperatures It is the core purpose of the present invention is to provide the remote sensor instrument and the receptacle accommodating the attractor being mutually disposed such that at least the bird's head is within a field of view of said remote sensor instrument.

It is another object of the present invention to provide the enclosure comprises at least one wall and at least one aperture.

It is another object of the present invention to provide the sections of the wall are a partial or whole wall, the wall characterized as being mesh, solid, see through, flexible, rigid or semi-rigid.

It is another object of the present invention to provide the attractor which is a food substance selected from the group consisting of solid food, liquid food and a combination thereof.

It is another object of the present invention to provide the remote sensing instrument which is a thermographic camera.

It is another object of the present invention to provide the system comprising a programmable memory unit configured to decipher readings acquired by the sensor.

It is another object of the present invention to provide the system comprising a processor programed to generate exact body temperature measurement from the readings.

It is another object of the present invention to provide the processor configured to communicate temperature measurements to a computer-readable medium.

It is another object of the present invention to provide the predefined surface which is adjacent to the eye and beak of said bird.

It is the object of the present invention to provide a method for measuring the body temperature of poultry comprising steps of: (a) providing a poultry house with a system for measuring temperature of birds; (b) attracting a bird by an attractor such that a bird's head is positioned within a receptacle; (c) generating thermal readings by a remote sensing instrument; and (d) calculating temperature measurement(s) from the acquired data. The step of generating said measurement(s) is provided by a weighted average of said readings and of the temperature measurement of each pixels within said reading.

It is another object of the present invention to provide the remote sensing instrument which is a thermographic camera.

It is another object of the present invention to provide the reading taken from a predefined surface, the surface adjacent to the eye and beak of the bird.

It is another object of the present invention to provide the reading further communicated to a computer-readable medium.

It is an object of the present invention to provide a system for regulating the environmental control system. The system comprises: (a) at least one arrangement for measuring bird's temperature; comprising at least one remote sensing instrument; (b) at least one programmable memory unit, the memory unit configured to decipher readings acquired by the remote sensing instrument; (c) at least one processor unit, the processor programed to generate exact temperature measurement from at the reading; (d) at least one control unit; the control unit programed to read temperature measurement and to generate instructions for climate control system; and (e) at least one communication module, the communication module configured to communicate instructions for regulating the temperature control system. The temperature measurement is a weighted average of the image and of the temperature measurement of each data point within each image.

It is another object of the present invention to provide the control unit configured to regulate the climate of said poultry house according to at least one parameter selected from the group consisting of: (a) average body temperature of individual birds; (b) number of birds whose body temperature is outside of a designated "comfort zone"; and (c) environmental readings.

It is another object of the present invention to provide the system also comprising at least one environmental control system.

It is another object of the present invention to provide the environmental control system consists of at least one technology selected from the group of technologies consisting of air conditioners, cooling pads, vitrines, heaters and ventilators.

It is another object of the present invention to provide the communication module configured to regulate the environmental control system of said poultry house.

It is another object of the present invention to provide the system configured to communicate with additional environmental or poultry sensors.

It is another object of the present invention to provide the environmental or poultry sensors selected from the group technologies comprising humidity, air temperature, light, and bird mass.

It is another object of the present invention to provide the system configured to identify the individual bird, the bird placing head to be measured.

It is another object of the present invention to provide the individual bird identified using a contact or contactless technology, the technology selected from a group consisting of radio frequency identification (RFID), magnetic trips, 2- or 3-dimensional bar codes and biometric identification.

It is another object of the present invention to provide the system also comprising an external temperature sensor configured to calibrate the remote sensor, selected from the group consisting of resistance thermometers, thermocouples or thermistors.

It is another object of the present invention to provide the climate regulated by said climate control unit meets requirements of European Council Directive 2007/43/EC of 28 Jun. 2007.

It is another object of the present invention to provide a method for regulating the temperature of poultry in a poultry house. The aforesaid method comprises steps of: (a) placing at least one arrangement for measuring the body temperature of the poultry in said poultry house; (b) placing at least one bird in the poultry house; (c) acquiring temperature measurements from at least one system; (d) communicating the measurement to climate control system of the poultry house; (e) regulating the climate of said poultry house by continuously measuring temperature of the birds in the poultry house; (f) wherein the temperature measurement is a weighted average of the measurements and of the temperature measurement of each pixels within said picture.

It is still another object of the present invention to provide a non-invasive system (10) for monitoring bird's temperature in poultry house, comprising a remote thermal sensor (14) configured to acquire a direct thermal reading of a specific predetermined organ of said bird (e.g., head, beak), thereby providing a local, reproducible, at least semi-continuous, noncontact and fast thermal readings; said accuracy is less than 2° C. in the range of 40 to 44° C.

Lastly, it is another object of the present invention to provide a method of providing poultry welfare in poultry house, said method comprising steps of monitoring bird's temperature by acquiring a local direct thermal reading of a specific predetermined organ of said bird (e.g., head, beak), by a remote thermal sensor (14); the accuracy of said sensor is less than 2° C. in the range of 40 to 44° C.

DETAILED DESCRIPTION OF THE PREFERRED EMBODIMENTS

It is the object of the current application to describe a system for measuring the temperature of a bird in a poultry house.

In the present application, the term "attractor" refers to a substance that attracts the bird to a specific position within the positioner. The attractor can work on sound, sight or smell. The substance could be a food or an instrument that generates a signal, such as a sound. In one preferred embodiment the attractor is a special food, such as seeds. The attractor can be placed inside a holder or receptacle to better position the birds head. The receptacle can be a hard, solid, container, such as a cup or a gentile pace holder, depending on the type of attractor.

In the present invention, the term "remote sensing instrument" refers to an instrument configured to acquire data about the bird without making contact. In one preferred embodiment the instrument is a thermographic camera.

Figure 1:
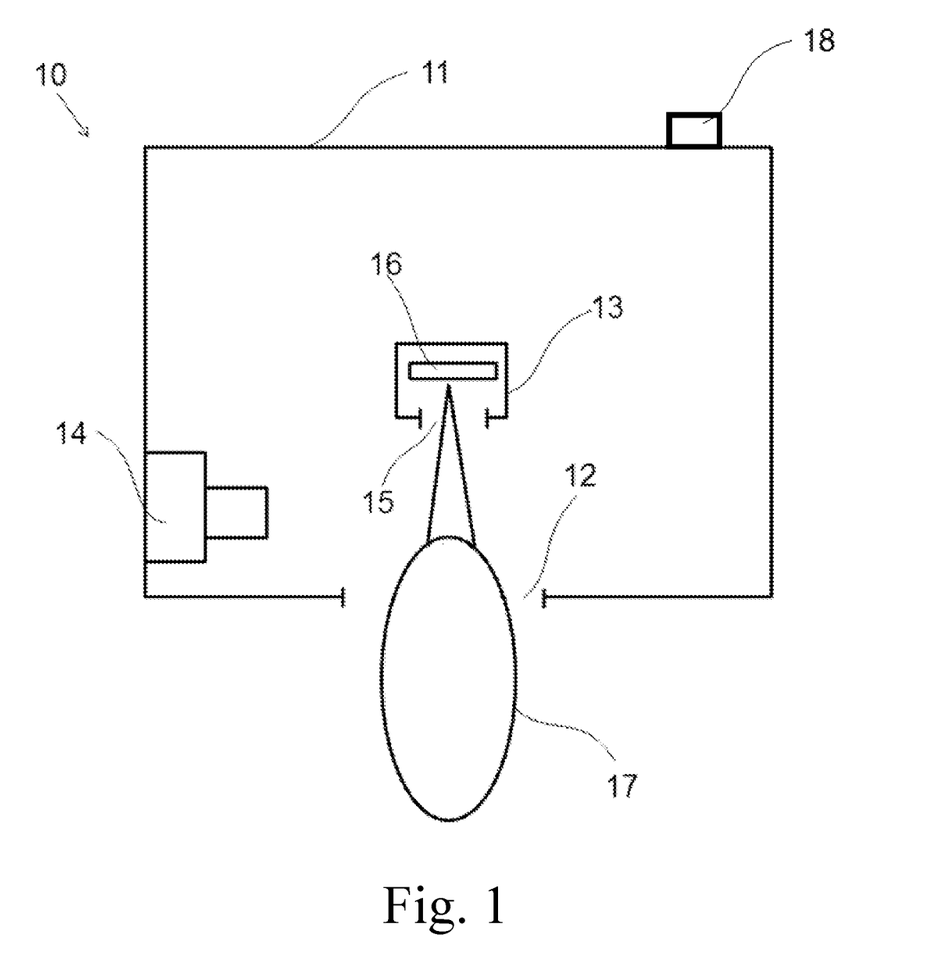
FIG. 1 is a schematic view of an arrangement for measuring bird temperature.

Reference is now made to FIG. 1 presenting a system (10) for measuring the temperature of birds in a poultry house. The system is constructed from an enclosure (11) that has at least one opening (12). The opening is configured to induce placing a bird's head (17) inside the enclosure (11) and reach an attractor (16) placed in a receptacle (13). Solid and liquid foods are in the scope of the present invention, A remote sensor instrument (14) and the receptacle (13) accommodating the attractor (16) are mutually disposed such that the bird's head (17) is within a field of view of the remote sensor instrument (14) in order to acquire a thermal reading of the bird, according to one embodiment, the remote sensor instrument (14) is a thermographic camera configured for taking at least one image of a specific area of birds' head near the eye and beak.

In one embodiment, the system also includes an external temperature sensor (18) that enables calibrating the remote sensing instrument (14). The temperature sensor selected from the group consisting of resistance thermometers (such as a PT100), thermocouples or thermistors. The calibration is conducted in real time and/or intermittently.

Figure 2:
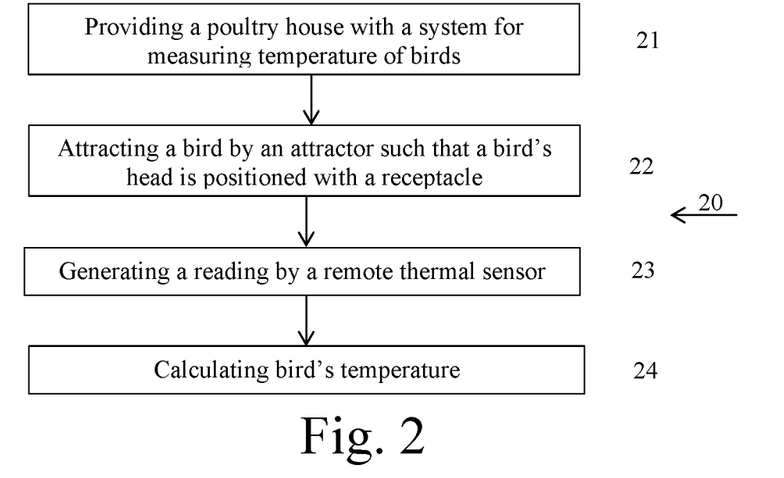
FIG. 2 is a flowchart of a method for measuring bird temperature.

Reference is now made to FIG. 2 presenting a method (20) for measuring the temperature of birds in a poultry house. The enclosure (21) is placed in a poultry house. When the bird is positioned in front of a remote sensor instrument (22) a reading of the bird is generated. The remote sensor instrument is configured to take multiple readings of a single bird. The reading(s) are entered into a computation system (23) that is configured to decode the reading and generate a temperature measurement (24). The computation system (23) generates measurements using multiple readings and multiple data points within each reading by using a weighted average of the readings and of the temperature measurement of each data point within each reading.

Figure 3:
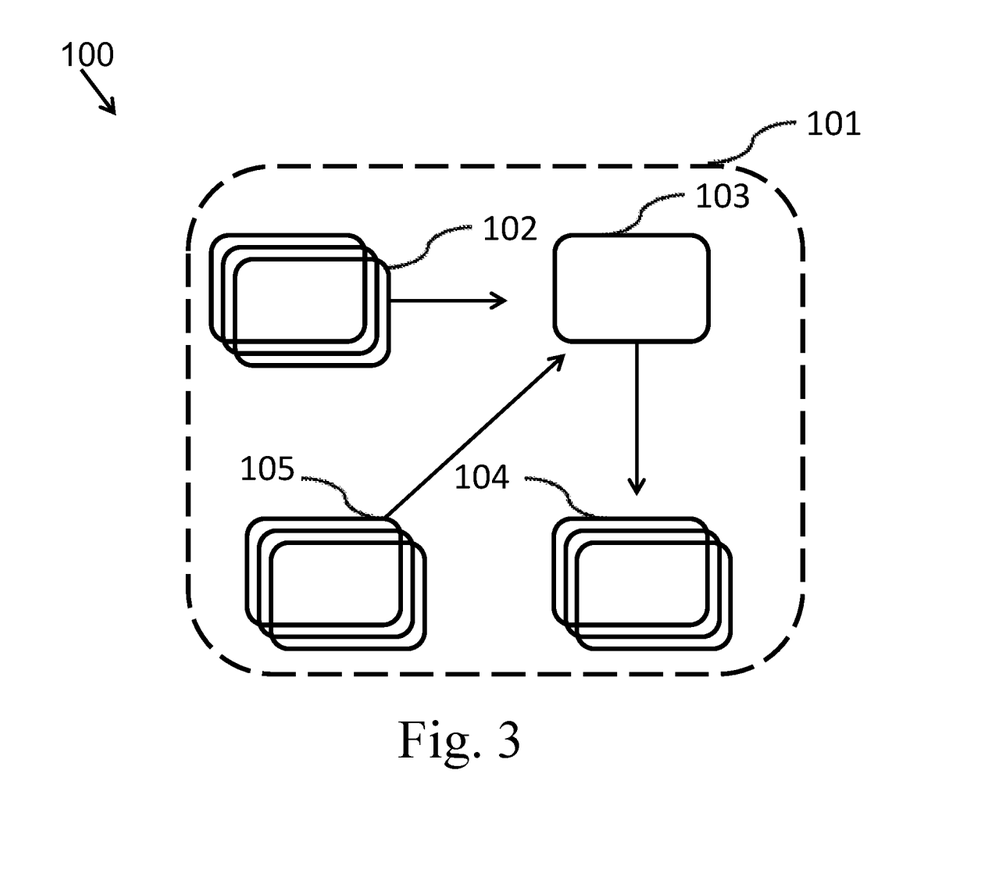
FIG. 3 is a schematic view of a system for controlling temperature in a poultry house.

Reference is now made to FIG. 3 presenting a system (100) for regulating the environmental conditions of a poultry house. The regulation system comprises a number of measuring modules (102) placed within a poultry house (101). The measuring modules are spread-out throughout the poultry house to enable a sampling of the poultry population in the house. The measuring modules (102) transmit the readings to a computation module (103). The computation module generates temperature measurements and regulates the environmental control units (104) placed throughout the poultry house. In one preferred embodiment of the current invention, the environmental control systems are air conditioners, cooling pads, vitrines, heaters and ventilators of all kinds. In another preferred embodiments the environment of the poultry house can be regulated by a combination of the various technologies listed above. The computation module (103) is configured to read input from additional sensors (105) that measure additional environmental parameters, such as air temperature, humidity etc.

Figure 4:
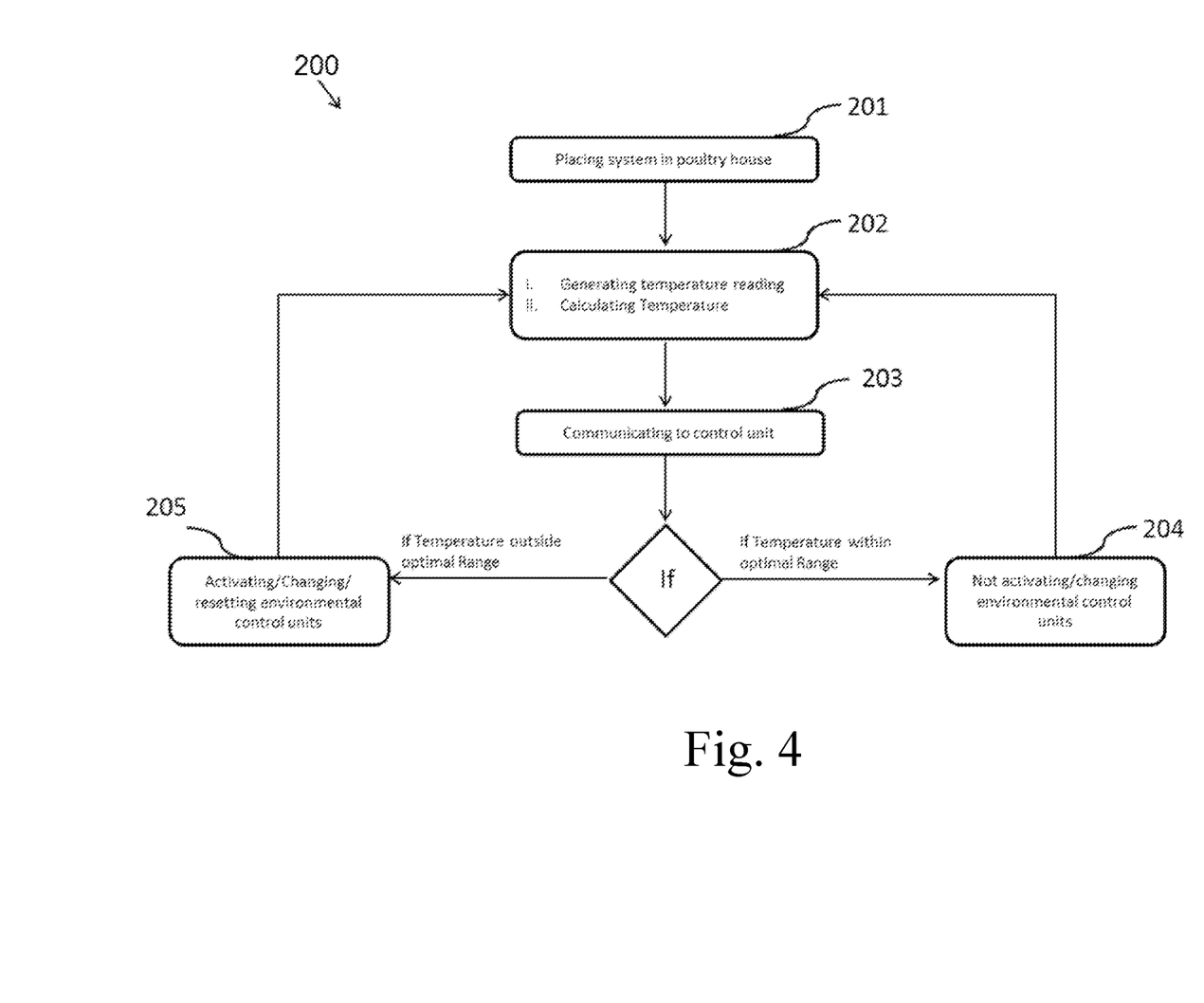
FIG. 4 is a flowchart of a method of controlling temperature in a poultry house.

Reference is now made to FIG. 4 presenting a method (200) for regulating the temperature in a poultry house. A measuring module (201) is placed in the poultry house, together with birds. A temperature reading in conducted (202.i) and the temperature is calculated (202.ii) and communicated to the control unit (203).

The control unit (203) is configured to regulate the poultry house climate according to various parameters: Average body temperature readings of individual birds; Number of birds whose body temperature is outside of a designated "comfort zone"; and Environmental readings.

In some embodiments, the control unit uses a combination of the listed parameters.

The settings are dependent on a number of variables, such as the species of bird in the poultry house, the outside climate, the season etc.

If the temperature is within the optimal range then the environmental control unit settings are not changed (204). If the temperature is outside the optimal range then the environmental control unit settings are recalculated (205). The steps of conducting temperature readings (202), communicating's the measurements to the controller (203) and resetting environmental control units (204, 205), are repeated to enable continuous regulation of the poultry house climate. Requirements to climate control are defined by European Council Directive 2007/43/EC of 28 Jun. 2007.

Figure 5:
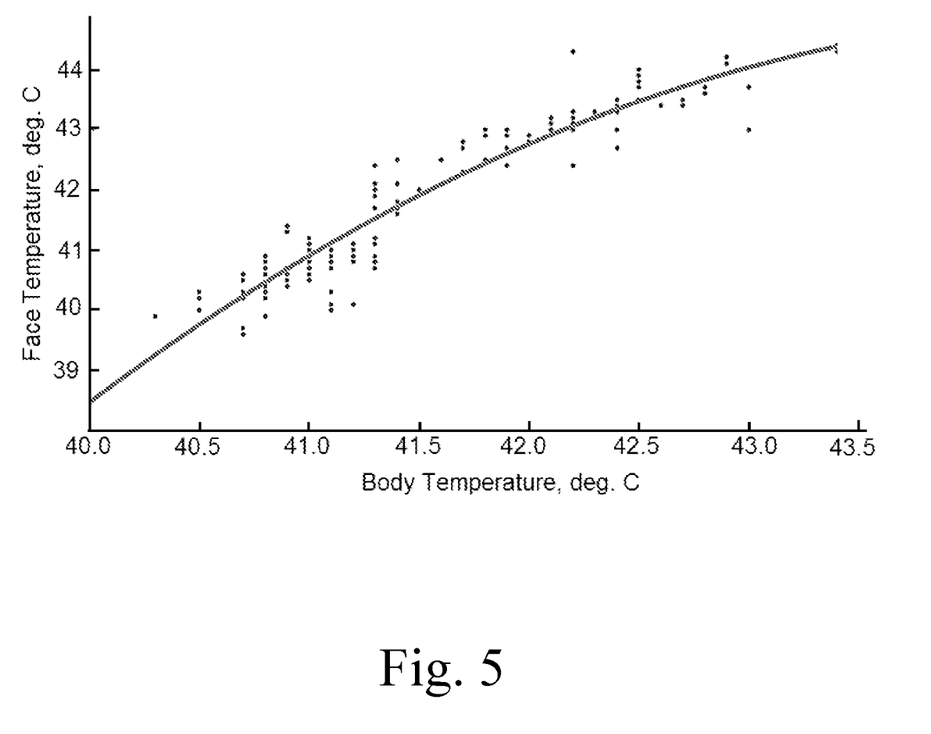
FIG. 5 is a graph illustrating correlation between model's prediction and logger temperature.
Figure 6:
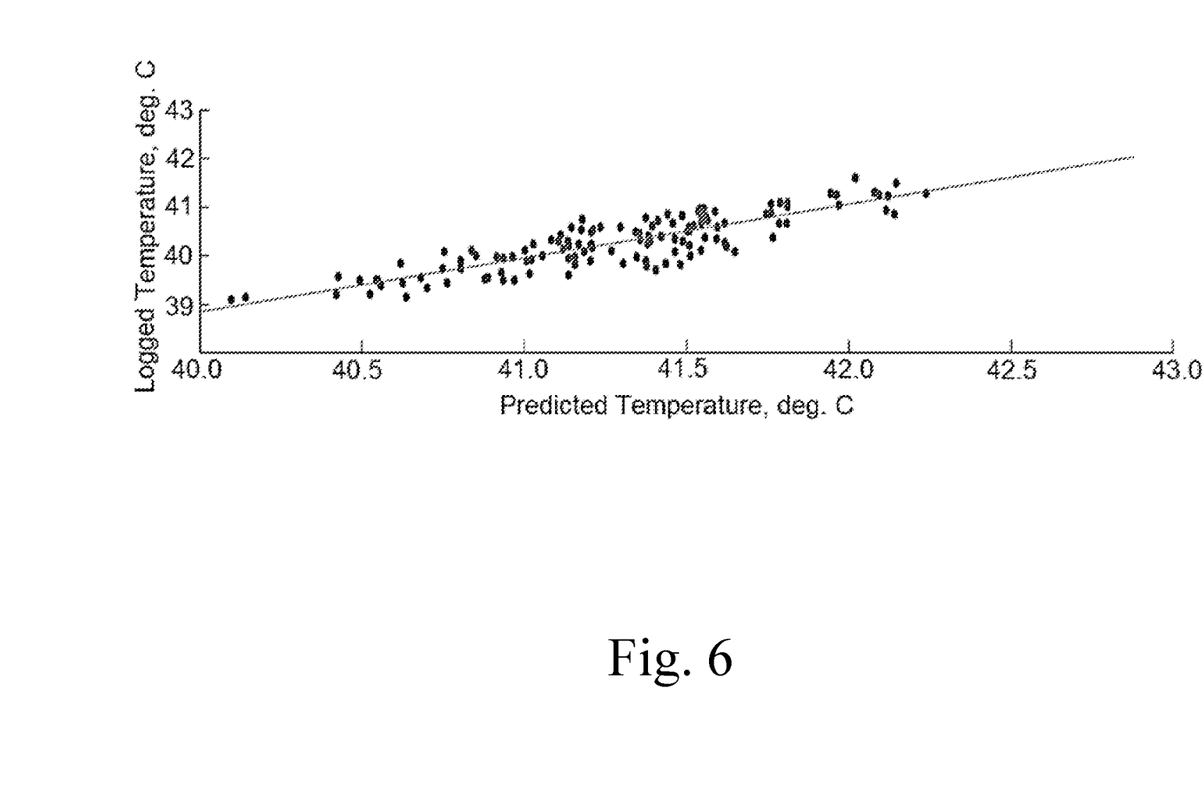
FIG. 6 is a graph illustrating correlation between face temperature and body temperature.

It is experimentally shown that the system of the present invention is able to sense the poultry body temperature in a production house and automate monitoring over a broiler stock without human intervention. By implanting temperature loggers and RFID tags into the birds, the thermal images of individual birds and the corresponding body temperature measured by the loggers were pared. Using the paired set of data consisting of logger temperatures and the matching thermal images, a model that predict body temperature of the bird by using a thermal image was built. FIG. 5 shows the correlation between face temperature and body temperature ($R^2=0.923478$). The model results, as seen in FIG. 6, confirm that body temperature can be measured using low cost thermal camera. This fact enables the future development of a thermal commercialized system.

The invention claimed is:

1. An arrangement (10) for measuring the body temperature of a bird, said system characterized by:
   a. an enclosure (11) having at least one aperture (12) configured for receiving a bird's head thereinto at least in a partial manner
   b. at least one receptacle (13) mounted within said enclosure (11); said at least one receptacle (13) accommodating an attractor (16);
   c. at least one remote sensing instrument (14) configured for acquire thermal reading and calculating bird's temperatures;
   wherein said remote sensor instrument (14) and the receptacle (13) accommodating the attractor (16) are mutually disposed such that at least the bird's head (17) is within a field of view of said remote sensor instrument (14).

2. The arrangement of claim 1, wherein at least one of the following is true:
   a. said enclosure comprises at least one wall and at least one aperture;
   b. said attractor is a food substance selected from the group consisting of solid food, liquid food and combination thereof;
   c. said remote sensing instrument is a thermographic camera;
   d. said system comprises a programmable memory unit configured to decipher readings acquired by said sensor;
   e. system comprises a processor programed to generate temperature measurement from said readings; and
   f. said predefined surface is adjacent to the eye and beak of said bird.

3. The arrangement of claim 2, wherein sections of said wall are a partial or whole wall, said wall characterized as being mesh, solid, see through, flexible, rigid or semi-rigid.

4. The arrangement of claim 2, wherein said processor is configured to communicate temperature measurements to a computer-readable medium.

5. A method (20) for measuring the body temperature of poultry comprising steps of;
   a. providing a poultry house with a system for measuring temperature of birds (21);
   b. attracting a bird by an attractor such that a bird's head is positioned within a receptacle (22);
   c. generating thermal readings by a remote sensing instrument (23); and
   d. calculating temperature measurements from said thermal readings (24);
   wherein said step of attracting said bird comprises positioning said bird such that such that at least the bird's head (17) is within a field of view of said remote sensor instrument (14).

6. The method of claim 5, wherein at least one of the following is true:
   a. said remote sensing instrument is a thermographic camera;
   b. said reading is taken from a predefined surface, said surface adjacent to the eye and beak of said bird; and
   c. said reading in further communicated to a computer-readable medium.

7. A system for regulating the environmental control system, said system comprising;
   a. at least arrangement for measuring bird's temperature; comprising at least one remote sensing instrument;
   b. at least one programmable memory unit, said memory unit configured to decipher readings acquired by said remote sensing instrument;
   c. at least one processor unit, said processor programed to generate exact temperature measurement from at said reading;
   d. at least one control unit; said control unit programmed to read temperature measurement and to generate instructions for climate control system; and
   e. at least one communication module, said communication module configured to communicate instructions for regulating said climate control system;
   wherein said temperature measurement is a weighted average of said data and of said temperature measurement of each data within said image.

8. The system of claim 7, wherein said control unit is configured to regulate the climate of said poultry house according to at least one parameter selected from the group consisting of:
   a. average body temperature of individual birds;
   b. number of birds whose body temperature is outside of a designated "comfort zone"; and
   c. environmental readings.

9. The system of claim 7, wherein said system also comprises at least one environmental control system.

10. The system of claim 9, wherein said environmental control system consists of at least one technology, said technologies selected from a group of technologies consisting of air conditioners, cooling pads, vitrines, heaters and ventilators of all kinds.

11. The system of claim 9, wherein said communication module is configured to regulate said environmental control system of said poultry house.

12. The system of claim 7, wherein at least one of the following is true:
   a. said system is configured to communicate with additional environmental or poultry sensors; and
   b. said system is configured to identify said individual bird, said bird placing head to be measured.

13. The system of claim 12, wherein said environmental or poultry sensors are selected from a group technologies comprising humidity, radiation, air temperature, light, and bird mass.

14. The system of claim 13, wherein said individual bird is identified using a contact or contactless technology, said technology selected from a group consisting of radio frequency identification (RFID), magnetic trips, 2- or 3-dimensional bar codes and biometric identification.

15. The system of claim 7, wherein said system also comprising an external temperature sensor configured to calibrate said remote sensor, said temperature sensor selected from a group consisting of resistance thermometers, thermocouples or thermistors.

16. The system according to claim 7, wherein said temperature regulated by said climate control unit meets requirements of European Council Directive 2007/43/EC of 28 Jun. 2007.

17. A method of regulating temperature of poultry in a poultry house, said method comprising steps of:
   a. placing at least one arrangement for measuring said body temperature of said poultry in said poultry house 201;
   b. placing at least one bird in said poultry house 202;
   c. acquiring temperature measurements from said system 203;
   d. communicating said measurement to climate control unit of said poultry house 204; and
   e. regulating climate of said poultry house by continuously measuring temperature of said birds in said poultry house 205;
   wherein said temperature measurement is a weighted average of said measurements and of said temperature measurement of each pixels within said picture.

18. The method according to claim 17, wherein said climate regulated by said climate control unit meets requirements of European Council Directive 2007/43/EC of 28 Jun. 2007.

19. A non-invasive system (10) for monitoring bird's temperature in poultry house, comprising a remote thermal sensor (14) configured to acquire a direct thermal reading of a specific predetermined organ of said bird, thereby providing a local, reproducible, at least semi-continuous, noncontact and fast thermal readings; said accuracy is less than 2° C. in the range of 40 to 44° C.

20. A method of providing poultry welfare in poultry house, said method comprising steps of monitoring bird's temperature by acquiring a local direct thermal reading of a specific predetermined organ of said bird by a remote thermal sensor (14); the accuracy of said sensor is less than 2° C. in the range of 40 to 44° C.

* * * * *